US 8,814,843 B2

(12) United States Patent
Van Bogart et al.

(10) Patent No.: US 8,814,843 B2
(45) Date of Patent: Aug. 26, 2014

(54) REUSABLE DIAPER LINER

(76) Inventors: Sarah B. Van Bogart, Andover, MN (US); Brian Van Bogart, Andover, MN (US)

(*) Notice: Subject to any disclaimer, the term of this patent is extended or adjusted under 35 U.S.C. 154(b) by 241 days.

(21) Appl. No.: 12/775,295

(22) Filed: May 6, 2010

(65) Prior Publication Data

US 2011/0276018 A1 Nov. 10, 2011

(51) Int. Cl.
*A61F 13/15* (2006.01)

(52) U.S. Cl.
USPC ............ 604/385.15; 604/385.14; 604/395; 604/397

(58) Field of Classification Search
USPC ............ 604/385.14, 385.15, 395, 397
See application file for complete search history.

(56) References Cited

U.S. PATENT DOCUMENTS

| | | | |
|---|---|---|---|
| 2,532,029 A * | 11/1950 | Medoff | 604/394 |
| 4,244,368 A * | 1/1981 | Caradonna | 604/398 |
| 4,961,736 A * | 10/1990 | McCloud | 604/385.15 |
| 5,032,119 A | 7/1991 | Hookano | |
| 5,069,672 A | 12/1991 | Wippler et al. | |
| 5,137,526 A | 8/1992 | Coates | |
| 5,181,915 A | 1/1993 | Smith | |
| 5,209,743 A | 5/1993 | Hardison | |
| 5,261,900 A | 11/1993 | Houle | |
| 5,261,901 A | 11/1993 | Guay | |
| 5,342,340 A | 8/1994 | Kichefski et al. | |
| 5,356,402 A | 10/1994 | Gillies et al. | |
| 5,368,585 A | 11/1994 | Dokken | |
| 5,409,476 A | 4/1995 | Coates | |
| 5,725,518 A | 3/1998 | Coates | |
| 6,579,273 B2 | 6/2003 | Dupuy | |
| 6,623,467 B1 | 9/2003 | Charles-Lundaahl | |
| 6,926,705 B1 * | 8/2005 | Coates | 604/385.19 |
| 7,914,507 B1 | 3/2011 | Magee | |
| 2005/0234420 A1 | 10/2005 | Artley | |
| 2009/0299313 A1 | 12/2009 | Knightingale | |
| 2011/0172622 A1 * | 7/2011 | Roe et al. | 604/368 |

FOREIGN PATENT DOCUMENTS

WO 2005051656 A1 6/2005

OTHER PUBLICATIONS

International Search Report and Written Opinion for related PCT application PCT/US2011/000784 dated Jul. 1, 2011 (10 pages).

* cited by examiner

*Primary Examiner* — Jacqueline F. Stephens
(74) *Attorney, Agent, or Firm* — Brooks, Cameron & Huebsch, PLLC

(57) ABSTRACT

The present disclosure provides reusable diaper liner devices, systems, and methods. In various embodiments, a reusable diaper liner can include an absorption layer that includes a first surface and a second surface, opposite the first surface. The reusable diaper liner also can include a waterproof layer that has a first surface and a second surface, opposite the first surface. The second surface of the absorption layer and the first surface of the waterproof layer can be positioned adjacent to each other and the reusable diaper liner can be configured to fit inside a diaper body.

20 Claims, 5 Drawing Sheets

REUSABLE DIAPER LINER

BACKGROUND

Diapers have been used to contain the waste of infants, toddlers, and in some cases, other individuals who do not have control of their bladders and/or bowel movements. Diapers can be made of a reusable fiber, such as cotton, and/or they can be made of disposable materials, such as plastic and cotton.

Disposable diapers can be made of a combination of plastics and soft fiber materials, such as cotton. The plastic can, for example, provide waterproof characteristics to prevent leakage through the soft fiber material portion. The soft fiber material portion can provide absorption for the waste of the wearer.

Disposable diapers have been readily available in most developed countries and can be desirable because the diaper can be disposed of in the trash without having to handle or dispose of the waste in the diaper separately. A disposable diaper can be disposed of after each time a diaper is soiled, no matter the quantity and type of waste. Thus the number of diapers used, and therefore, the cost of buying disposable diapers is not dependent on the quantity of type of waste that soils a diaper.

However, disposable diapers can be undesirable, for example, because the chemicals used to make the diapers can be harmful to the wearer. Also, disposable diapers can create strain on the environment because a diaper is disposed of in the trash each time a wearer creates waste while wearing a disposable diaper and these types of diapers are not typically readily degradable.

In contrast, reusable diapers can be desirable because of the reduced harmful environmental impact over disposable diapers, the ability to choose chemical-free materials, and the reduced overall cost due to the fixed cost of buying fewer diapers and reusing them. However, the initial cost of a reusable diaper system can, in many instances, have a larger initial investment when compared to disposable systems. Balancing the desirable and undesirable characteristics of the reusable and disposable diapers can be difficult. The conveniences of disposable diapers make them very popular, as evidenced by the 40 million diapers that are disposed of in the United States every day. Many disposable diaper users would like to use reusable diapers, but do not because of the conveniences of using disposable diapers and the difficulties, such as the expense and inconvenience, of using both disposable and reusable diapers.

DETAILED DESCRIPTION

Figure 1:
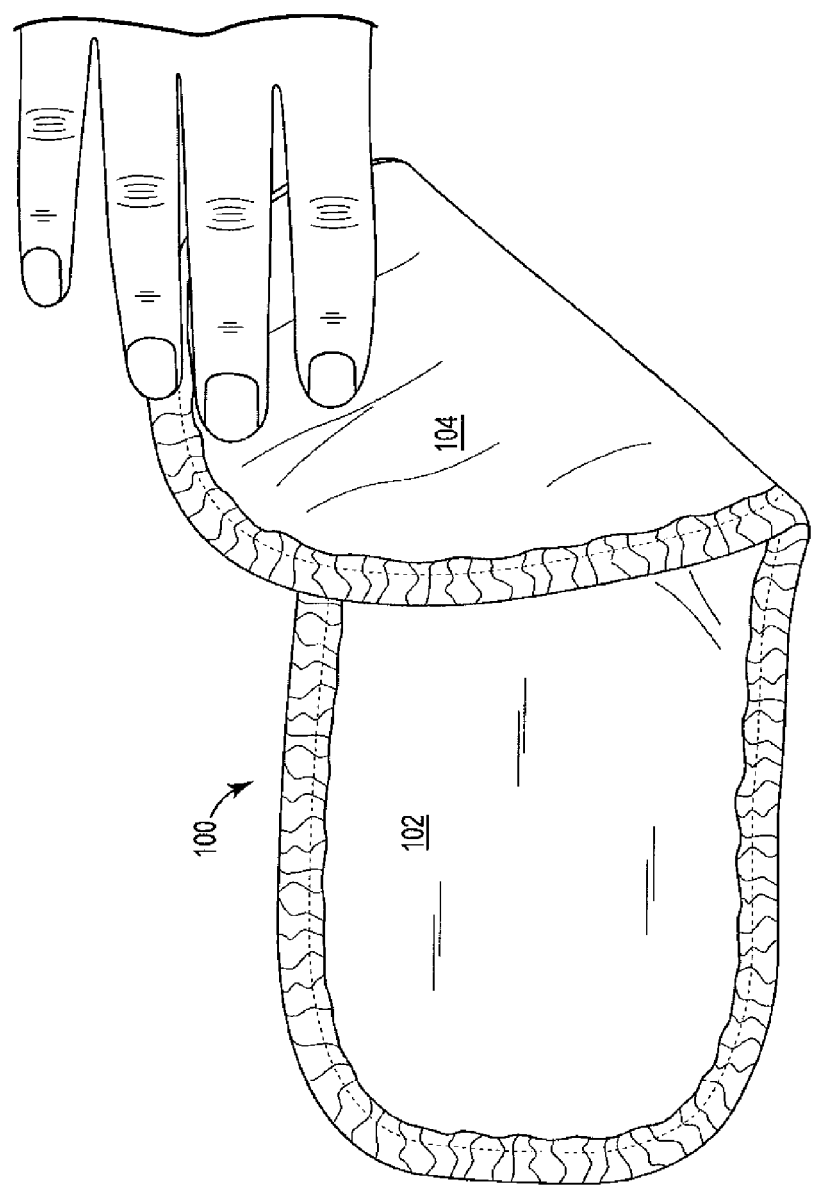
FIG. 1 illustrates a reusable diaper liner viewed showing a portion of an absorption layer and a portion of a waterproof layer according to an embodiment of the present disclosure.

The present disclosure provides reusable diaper liner devices, systems, and methods. Embodiments of the present disclosure can be used with diaper bodies that can be disposable diapers and/or reusable diaper components. Accordingly such liners can provide numerous benefits as will be understood by those of ordinary skill in the art some of which are described herein.

In various embodiments, the diaper body can be a reusable diaper shell, such as a reusable diaper cover, and/or a disposable diaper, among other suitable diaper bodies. Reusable diaper covers/shells can be part of a reusable diaper system and can include a waterproof layer, an absorption layer, a waterproof layer and an absorption layer. In various embodiments, an absorption layer can include a number of layers of material and a waterproof layer can include a number of layers of material.

In various embodiments, a reusable diaper liner can include an absorption layer that includes a first surface and a second surface, opposite the first surface. The reusable diaper liner also can include a waterproof layer that has a first surface and a second surface, opposite the first surface. The second surface of the absorption layer and the first surface of the waterproof layer can be positioned adjacent to each other and the reusable diaper liner can be configured to fit inside a diaper body.

In one or more embodiments, the absorption layer and the waterproof layer can be coupled together at their respective perimeters. In some embodiments, an absorption insert can be placed between the absorption layer and the waterproof layer. The perimeter of the absorption layer and waterproof layer can include an opening configured to receive and remove the absorption insert.

In one or more embodiments, the first surface of the waterproof layer can be coupled to the first surface of the absorption layer at the perimeter of each layer. In some embodiments, the perimeter of the waterproof layer includes an elastic gusset configured to contain waste within the reusable diaper liner. The absorption layer can be made of fleece, bamboo, and/or cotton, among other materials, and the waterproof layer can be made of polyurethane laminate (PUL), among other materials.

In various embodiments, a diaper system can include a diaper body having an outer layer and an inner layer and a reusable diaper liner, wherein the reusable diaper liner includes an absorption layer that includes a first surface and a second surface opposite the first surface and a waterproof layer that includes a first surface and a second surface opposite the first surface. The second surface of the absorption layer and the first surface of the waterproof layer are positioned adjacent to each other. In one or more embodiments, the second surface of the waterproof layer of the reusable diaper liner can be adjacent to the inner layer of the diaper body.

Various embodiments can include a method of using a diaper system by placing a first reusable diaper liner adjacent to an inner surface of a diaper body, placing the first reusable diaper liner and the diaper body on a wearer, removing the diaper body and the first reusable diaper liner from the wearer when the first reusable diaper liner becomes soiled and removing the first reusable diaper liner from the inner surface of the diaper body, placing a second reusable diaper liner adjacent to an inner surface of the diaper body, and placing the second reusable diaper liner and the diaper body on a wearer.

In one or more embodiments, the method can include washing the first reusable diaper liner after the first reusable diaper liner becomes soiled. Also, the diaper body and the second reusable diaper liner can be removed from the wearer when the second reusable diaper liner becomes soiled. The second reusable diaper liner can be removed from the inner surface of the diaper body and the first reusable diaper liner can be placed adjacent to an inner surface after washing the first reusable diaper liner. The first reusable diaper liner and the diaper body can be placed on a wearer.

In some embodiments, the first reusable diaper liner can be replaced by the second reusable diaper liner in the diaper body a number of times and the second reusable diaper liner can replace the first reusable diaper liner in the diaper body a number of times. Also, the diaper body can be replaced with a clean diaper body when the inner surface of the diaper body becomes soiled.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process and/or structural changes may be made without departing from the scope of the present disclosure.

The Figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2.

As will be appreciated, elements shown in the various embodiments herein can be added, exchanged, and/or eliminated so as to provide a number of embodiments of the present disclosure. In addition, the proportion and the relative scale of the elements provided in the figures are intended to illustrate various embodiments of the present disclosure and are not to be used in a limiting sense.

FIG. 1 illustrates a reusable diaper liner 100 viewed showing a portion of an absorption layer 102 and a portion of a waterproof layer 104 according to an embodiment of the present disclosure. In the embodiment of FIG. 1, the absorption layer 102 is typically made from a soft material as the layer may be in contact with a wearer. For example, the absorption layer 102 of the reusable diaper liner 100 can be made of fleece material, however, any other suitable material may be used in various embodiments. In some embodiments, the absorption layer 102 can be coupled to a waterproof layer 104 along its perimeter by a coupling mechanism, such as thread or other suitable mechanisms to attach the layers together.

Among other benefits, the absorption layer 102 can, for example, be used to absorb and contain waste from a wearer. The waterproof layer 104 can, for example, prevent waste from contacting a diaper body's inner surface or from leaking outside of a diaper body. The absorption layer 102 can include a number of layers of material and the waterproof layer 104 can include a number of layers of material.

Figure 2:
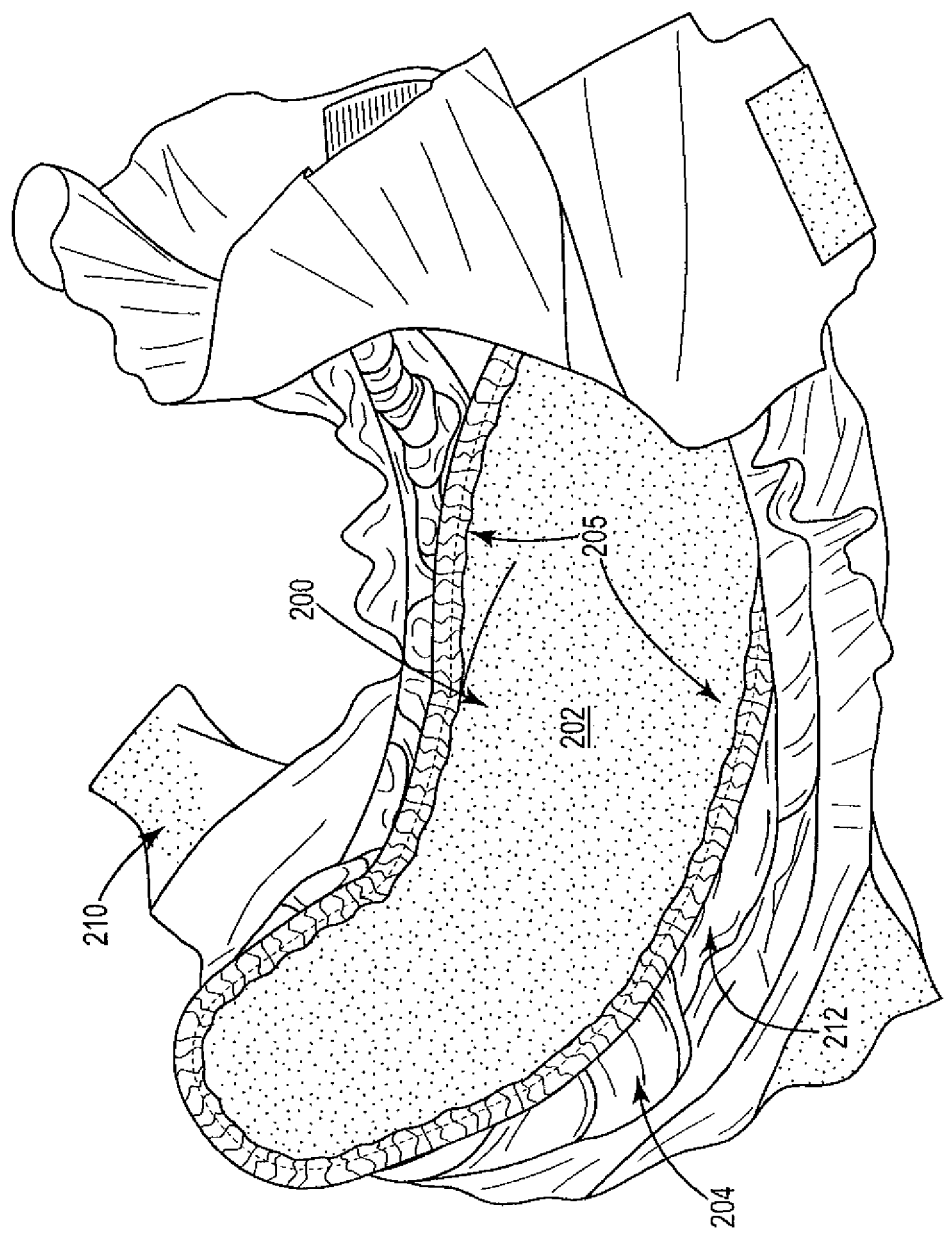
FIG. 2 illustrates a reusable diaper liner positioned in a diaper body according to an embodiment of the present disclosure.

FIG. 2 illustrates a reusable diaper liner positioned in a diaper body according to an embodiment of the present disclosure. In FIG. 2, the reusable diaper liner 200 is placed inside the diaper body 210 adjacent to the inner surface 212 of the diaper body 210.

In some embodiments, the diaper liner 200 can be fixed to the inside of the diaper body 210. This can be accomplished in any suitable manner (e.g., via snaps, hook and loop fasteners (Velcro), releasable adhesive, among others).

In the embodiment of FIG. 2, the waterproof layer 204 of the reusable diaper liner 200 is in contact with the inner surface 212 of the diaper body 210. When the reusable diaper liner 200 is placed within the diaper body 210, the absorption layer 202 can become the layer that contacts and contains the waste of a wearer. Thus preventing waste from contacting the inner surface 212 or outer surface 214 of the diaper body and therefore allowing the diaper body to be reused multiple times.

Once a reusable diaper liner 200 is soiled, the soiled reusable diaper liner 200 can be removed from the diaper body 210 and washed. The cleaned reusable diaper liner or a different reusable diaper liner can then be placed in the diaper body allowing the diaper body to be used again. As discussed above this allows a single diaper body to be used with a number of clean reusable diaper liners until the diaper body becomes soiled, e.g., the reusable diaper liner was not able to contain all of the waste from a user, and the diaper body needs to either be washed if the diaper body was a reusable diaper body or disposed of if the diaper body was a disposable diaper.

In some embodiments, the reusable diaper liner 200 can include an elastic gusset 205 at the perimeter to contain the waste on and in the reusable diaper liner 200.

Figure 3:
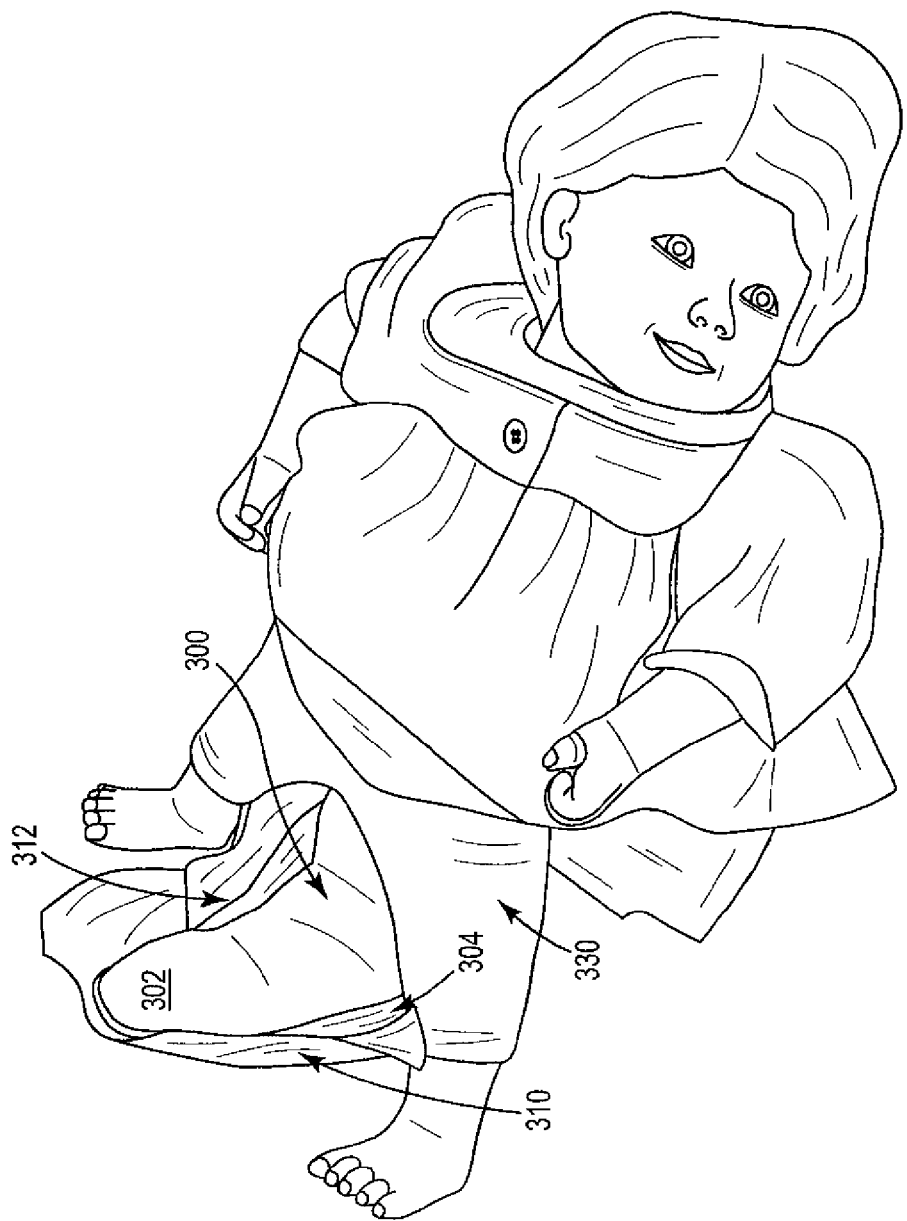
FIG. 3 illustrates a reusable diaper liner positioned in a diaper body partially applied as it would be to a wearer according to an embodiment of the present disclosure.

FIG. 3 illustrates a reusable diaper liner positioned in a diaper body partially applied as it would be to a wearer according to an embodiment of the present disclosure. In FIG. 3, the reusable diaper liner 300 is placed inside the diaper body 310 adjacent to the inner surface 312 of the diaper body 310. The waterproof layer 304 of the reusable diaper liner 300 is in contact with the inner surface 312 of the diaper body 310 and the absorption layer 302 can become the layer that contacts the wearer 330 and contains the waste of the wearer 330. Such embodiments can also be beneficial in allowing someone interested in trying reusable diapers to see some of the benefits without having to fully convert from a disposable system to a reusable system.

Figure 4:
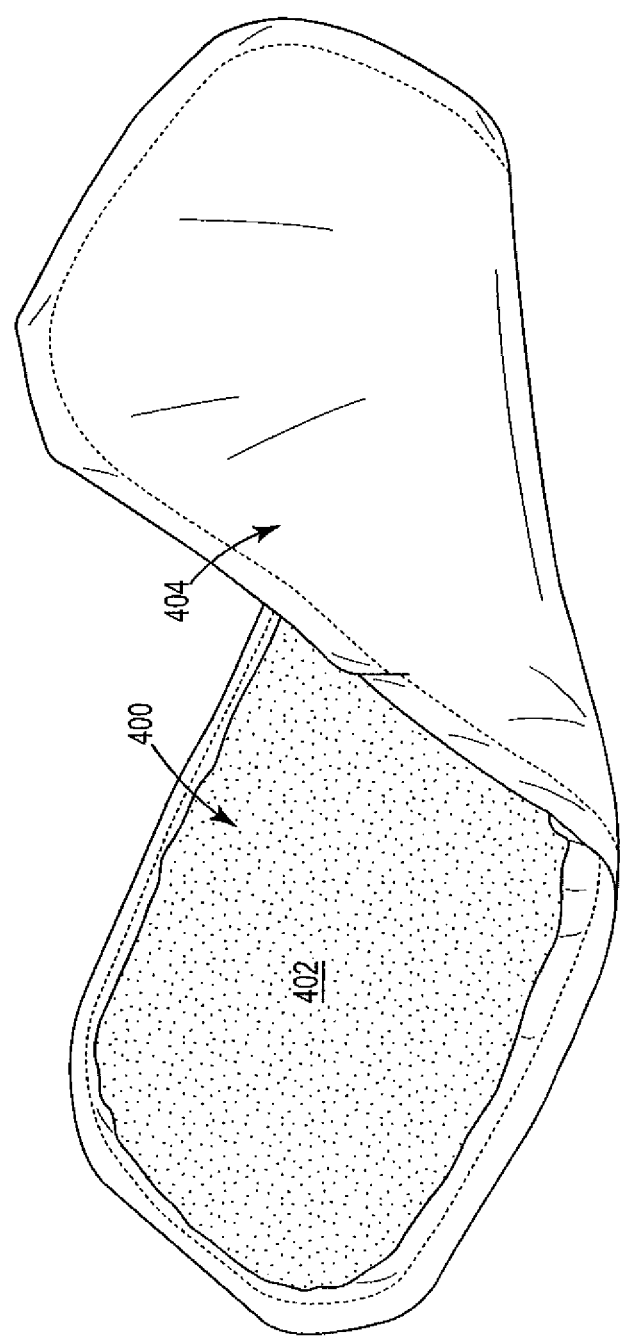
FIG. 4 illustrates a reusable diaper liner viewed showing a portion of an absorption layer and a portion of the waterproof layer according to an embodiment of the present disclosure.

FIG. 4 illustrates a reusable diaper liner 400 viewed showing a portion of an absorption layer and a portion of the waterproof layer according to an embodiment of the present disclosure. In FIG. 4, the waterproof layer 404 can be coupled to the absorption layer 402 by wrapping around the edge of the absorption layer 402, therefore a portion of the exposed surface of the absorption layer near the perimeter is covered by the waterproof layer 404. This barrier of the waterproof layer 404 near the perimeter of the exposed portion of the absorption layer 402 can, for example, be beneficial by containing waste within the exposed surface of the absorption layer 402.

Figure 5:
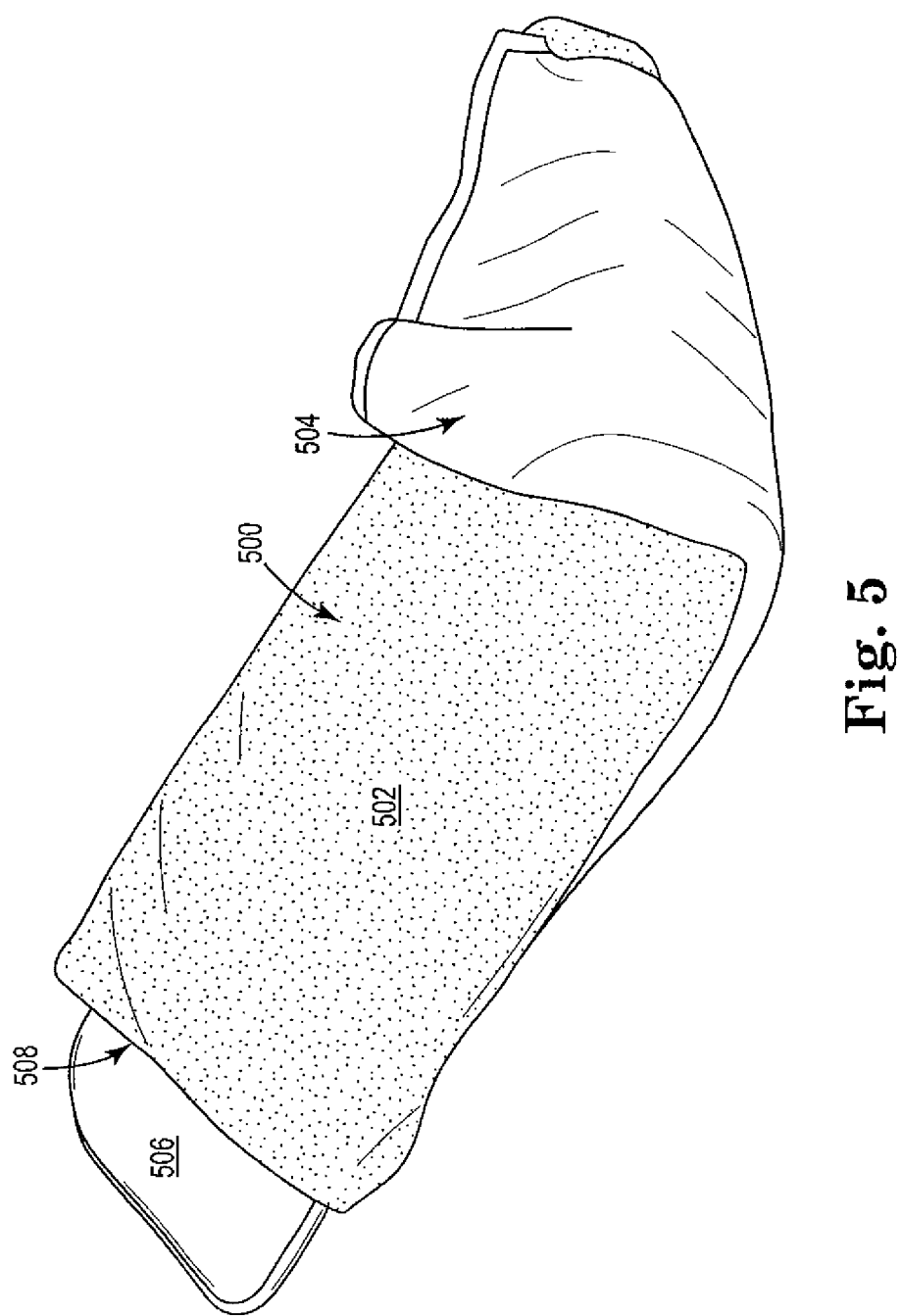
FIG. 5 illustrates a reusable diaper liner viewed showing a portion of an absorption layer, a portion of a waterproof layer, a portion of an absorption insert according to an embodiment of the present disclosure.

FIG. 5 illustrates a reusable diaper liner 500 viewed showing a portion of an absorption layer, a portion of a waterproof layer, a portion of an absorption insert according to an embodiment of the present disclosure. In FIG. 5, an absorption insert 506 is placed between the absorption layer 502 and the waterproof layer 504 through opening 508. Opening 508 can provide access for adding and removing the absorption insert 506.

In various embodiments, an absorption insert can be placed between the absorption and waterproof layer. In such embodiments, the absorption layer and the absorption insert can combine to absorb and contain the waste of a wearer. In such embodiments, the absorption layer and absorption insert can be laundered after the reusable diaper liner has been soiled. The absorption insert between the absorption and waterproof layer can prevent and/or limit waste from soiling the diaper body, thereby reducing the need to replace the diaper body each time the reusable diaper liner is soiled.

The absorption insert between the absorption and waterproof layers can be used as a back-up to the absorption layer for large amounts of waste that the absorption layer cannot absorb on its own.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

Although specific embodiments have been illustrated and described herein, those of ordinary skill in the art will appreciate that an arrangement calculated to achieve the same techniques can be substituted for the specific embodiments shown. Combination of the above embodiments, and other embodiments not specifically described herein will be apparent to those of skill in the art upon reviewing the above description. The scope of the various embodiments of the invention includes other applications in which the above structures and methods can be used. Therefore, the scope of various embodiments of the invention should be determined with reference to the appended claims, along with the full range of equivalents to which such claims are entitled.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the invention require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The present disclosure provides reusable diaper liner devices, systems, and methods. In various embodiments, a reusable diaper liner can include an absorption layer that includes a first surface and a second surface, opposite the first surface. The reusable diaper liner also can include a waterproof layer that has a first surface and a second surface, opposite the first surface. The second surface of the absorption layer and the first surface of the waterproof layer can be positioned adjacent to each other and the reusable diaper liner can be configured to fit inside a diaper body.

What is claimed is:

1. A reusable diaper liner, comprising:
   an absorption layer, wherein the absorption layer is reusable and includes a first surface and a second surface opposite the first surface; and
   a waterproof layer, wherein a perimeter of the waterproof layer includes an elastic gusset, wherein a perimeter of the absorption layer is coupled to the perimeter of the waterproof layer proximate to the elastic gusset, wherein the waterproof layer is reusable and includes a first surface and a second surface opposite the first surface, wherein the second surface of the absorption layer and the first surface of the waterproof layer are positioned adjacent to each other, and wherein at least a portion of the perimeter of waterproof layer of the reusable diaper liner is positioned inside a diaper body and adjacent to an inner surface of the diaper body.

2. The reusable diaper liner of claim 1, wherein the absorption layer and the waterproof layer are coupled together at their respective perimeters.

3. The reusable diaper liner of claim 1, wherein an absorption insert is located between the absorption layer and the waterproof layer.

4. The reusable diaper liner of claim 3, wherein the reusable diaper liner includes an opening configured to receive and remove the absorption insert.

5. The reusable diaper liner of claim 3, wherein the absorption layer is made of a material selected from the group including fleece, bamboo, and cotton.

6. The reusable diaper liner of claim 1, wherein the first surface of the waterproof layer is coupled to the first surface of the absorption layer at a perimeter of the reusable diaper liner.

7. The reusable diaper liner of claim 1, wherein absorption layer and the waterproof layer are coupled together at their respective perimeters and the perimeter of the waterproof layer includes an elastic gusset.

8. A diaper system, comprising:
   a diaper body having an outer layer and an inner layer; and
   a reusable diaper liner positioned adjacent to the inner layer of the diaper body, wherein the reusable diaper liner includes an absorption layer that is reusable and includes a first surface and a second surface opposite the first surface and a waterproof layer that includes a first surface and a second surface opposite the first surface; wherein the second surface of the absorption layer and the first surface of the waterproof layer are positioned adjacent to each other; and wherein a perimeter of the waterproof layer includes an elastic gusset, a perimeter of the absorption layer is coupled to the perimeter of the waterproof layer proximate to the elastic gusset, and at least a portion of the perimeter of the waterproof layer is positioned adjacent to the inner layer of the diaper body.

9. The diaper system of claim 8, wherein the second surface of the waterproof layer of the reusable diaper liner is adjacent to the inner layer of the diaper body.

10. The diaper system of claim 8, wherein the reusable diaper liner includes the elastic gusset at the edge of the reusable diaper liner configured to contain waste within the reusable diaper liner.

11. The diaper system of claim 8, wherein the reusable diaper liner includes an absorption insert positioned between the absorption layer and the waterproof layer.

12. The diaper system of claim 11, wherein the absorption insert is removable from the reusable diaper liner via an opening in the reusable diaper liner.

13. The diaper system of claim 8, wherein the absorption layer is held adjacent to the first surface of the waterproof layer by the elastic gusset.

14. The diaper system of claim 8, wherein the absorption layer is made of a material selected from the group including fleece, bamboo, and cotton.

15. A method of using a diaper system, comprising:
    placing a first reusable diaper liner, having a reusable absorption layer, adjacent to an inner surface of a diaper body, where a waterproof layer of the first reusable diaper liner is reusable and includes a perimeter having an elastic gusset, a perimeter of the reusable absorption layer is coupled to the perimeter of the waterproof layer proximate to the elastic gusset, and at least a portion of the perimeter of the waterproof layer is positioned adjacent to the inner surface of the diaper body;
    placing the first reusable diaper liner and the diaper body on a wearer;
    removing the diaper body and the first reusable diaper liner from the wearer when the first reusable diaper liner becomes soiled and removing the first reusable diaper liner from the inner surface of the diaper body;
    placing a second reusable diaper liner adjacent to an inner surface of the diaper body, where a waterproof layer of the second reusable diaper liner is positioned adjacent to the inner surface of the diaper body; and
    placing the second reusable diaper liner and the diaper body on a wearer.

16. The method of claim 15, wherein the method includes washing the first reusable diaper liner after the first reusable diaper liner becomes soiled.

17. The method of claim 15, wherein the method includes removing the diaper body and the second reusable diaper liner from the wearer when the second reusable diaper liner becomes soiled, removing the second reusable diaper liner from the inner surface of the diaper body, placing the first reusable diaper liner adjacent to an inner surface after washing the first reusable diaper liner, and placing the first reusable diaper liner and the diaper body on a wearer.

18. The method of claim 15, wherein the method includes replacing the first reusable diaper liner for the second reusable diaper liner in the diaper body a number of times.

19. The method of claim 15, wherein the method includes replacing the second reusable diaper liner for the first reusable diaper liner in the diaper body a number of times.

20. The method of claim 15, wherein the diaper body is a disposable diaper and the method includes disposing of the disposable diaper when the inner surface of the disposable diaper becomes soiled.

\* \* \* \* \*